United States Patent [19]

Webb et al.

[11] Patent Number: 5,243,061
[45] Date of Patent: Sep. 7, 1993

[54] METHOD FOR MAKING ORGANOHALOSILANES

[75] Inventors: Steven W. Webb, Clifton Park; Alan Ritzer, Sand Lake; John D. Neely, Clifton Park, all of N.Y.

[73] Assignee: General Electric Company, Schenectady, N.Y.

[21] Appl. No.: 987,872

[22] Filed: Dec. 9, 1992

[51] Int. Cl.⁵ .............................................. C07F 7/16
[52] U.S. Cl. ..................................... 556/472; 556/473
[58] Field of Search ................ 556/472, 473; 423/341, 423/342

[56] References Cited

U.S. PATENT DOCUMENTS

| | | | |
|---|---|---|---|
| 4,314,908 | 2/1982 | Downing et al. | 556/472 X |
| 4,450,282 | 5/1984 | Ritzer et al. | 556/472 |
| 4,758,352 | 7/1988 | Feldner et al. | 210/719 |
| 4,960,523 | 10/1990 | Degen et al. | 210/721 |
| 5,000,934 | 3/1991 | Marko et al. | 423/335 |
| 5,059,706 | 10/1991 | Degen et al. | 556/472 |

OTHER PUBLICATIONS

The Chemistry of Silicon, E. G. Rochow, Chapter 15 of Comprehensive Inorganic Chemistry, Pergamon Press, Metallic Silicides and Silicon Alloys, p. 1361, (1964).

*Primary Examiner*—Arthur C. Prescott
*Attorney, Agent, or Firm*—William A. Teoli; William H. Pittman

[57] ABSTRACT

A method for making organohalosilanes is provided utilizing spent contact mass generated during the production of organohalosilanes by the direct method which has been treated in an oxygen containing atmosphere to render it non-pyrophoric in air.

7 Claims, No Drawings

METHOD FOR MAKING ORGANOHALOSILANES

CROSS REFERENCE TO RELATED APPLICATION

Reference is made to copending application RD-22,497, which is filed concurrently herewith.

BACKGROUND OF THE INVENTION

The present invention relates to a method for making organohalosilanes by the direct reaction of an organic halide such as methylchloride and powdered silicon in the presence of a copper catalyst. More particularly, the present invention relates to the employment of thermally oxidized spent direct method contact mass as a source of copper oxide catalyst for the production of organohalosilanes.

Prior to the present invention, organohalosilanes were generally made by the direct reaction of an organic halide and powdered silicon in the presence of a copper catalyst as shown by Rochow U.S. Pat. No. 2,380,995. It was found that as the reaction proceeded, the silicon powder became spent which adversely affected yield and selectivity.

Rossmy, U.S. Pat. No. 3,069,452 teaches that improved yields and selectivity of organohalosilanes can be obtained if the copper catalyst used in the Rochow synthesis is replaced with a brittle easily grindable silicon-copper alloy having from 50% to 99% by weight copper. The silicon copper alloy is then finely ground and mixed with silicon powder and the resulting mixture is sintered in an inert atmosphere prior to reaction with organic halide.

In Shade, U.S. Pat. No. 4,281,149, particles of silicon and copper of less than 40 microns average diameter which were generated during the Rochow process are removed from the reactor, abraded and then returned to the reactor. In Shah et al, U.S. Pat. No. 4,307,242, a portion of direct process contact mass is analyzed for particle size distribution, classified and segregated into a silicon rich fraction which can be returned to the reactor, and a silicon poor fraction which can be removed from the reactor.

In copending application Ser. No. 7/867,657, filed Apr. 13, 1992, there is described a method for passivating or stabilizing spent silicon contact mass generated during the direct method for making organohalosilanes by the reaction between silicon powder and an organic halide such as methylchloride. Spent silicon contact mass can have an average particle size in the range of 0.1 to 200 microns. It is difficult to manage because it is pyrophoric in air and cannot be readily moved to an appropriate waste disposal site or be reused. Treatment of spent silicon contact mass by heating it at a temperature in the range of about 900° C. to about 1400° C. under an inert atmosphere has been found to render the spent contact mass substantially unreactive in air and more easily handled. The treating procedure of copending application Ser. No. 07/867,657, provides a significant advance over prior art methods such as shown by Hosokawa, U.S. Pat. No. 4,724,122, requiring the combining of the spent silicon contact mass with water and granulating the mixture followed by coating the resulting granules with an inert organic powder. Offenlegungschrift DE 313 1732A1 and U.S. Pat. No. 4,758,35to Feldner et al. also describe procedures for reprocessing residues produced during organohalosilane synthesis. Unlike copending application serial no. 07/867,657, the residues from DE 313 1732A1 and U.S. Pat. No. 4,758,352 are derived from sludge vessels which consist of siliceous solids and liquids such as polysilanes. It is desirable therefore to provide additional procedures for making organohalosilane from spent powders while minimizing waste.

SUMMARY OF THE INVENTION

The present invention is based on the discovery that spent direct method contact mass which has been thermally treated in an oxygen containing atmosphere, such as air, oxygen or steam, at temperatures sufficient to render it substantially nonreactive in air, can be recycled and used with organic halide either directly or in combination with silicon powder and direct method catalyst to generate additional organohalosilanes.

STATEMENT OF THE INVENTION

There is provided by the present invention, a process for making organohalosilanes by the direct method, comprising effecting reaction between an organic halide and a mixture comprising silicon powder, an effective amount of direct method catalyst, and spent direct method contact mass which has been in an oxygen containing atmosphere under conditions sufficient to render it substantially nonreactive in air at temperatures up to 350° C., where the resulting treated spent direct method contact mass is used directly or in combination with silicon powder and direct method catalyst in an amount sufficient to maintain during organohalosilane production, from about 0.1 to about 10% by weight of copper relative to silicon.

The spent contact mass treated in accordance with the practice of the method of the present invention can have a particle size in the range of from 0.1 to 200 microns. Treatment of the spent contact mass can be effected at temperatures in the range of about 200° C. to about 800° C. under an oxygen containing atmosphere. The spent silicon contact mass which can be treated in accordance with the present invention and further employed in generating organohalosilanes can have a surface area of up to about 25 m²/g. Spent silicon contact mass which can be treated and used in the generation of organohalosilanes in accordance with the invention include materials shown by Marko et al, U.S. Pat. No. 5,000,934, Hosokawa, U.S. Pat. No. 4,724,122 and Ritzer et by reference.

In the practice of the preferred form of the invention, spent silicon contact mass is treated after it has been collected from an organohalosilane reactor, and recycled with powdered silicon and direct method catalyst which hereinafter means copper catalyst, or a mixture of copper catalyst and one or more promoters such as zinc. Suitable copper catalysts include carboxylic acid salts of copper, such as copper formate, partially oxidized copper as well as copper salts such as cupric chloride, cuprous chloride, and copper metal particulate. Promoters which can be employed with copper catalyst are zinc metal, zinc dust or a zinc compound such as zinc oxide. Other promoters include tin metal, and tin compounds, such as tin oxide and tin halides such as tin tetrachloride.

If desired the spent silicon contact mass can be treated and stored prior to being recycled in the organohalosilane reactor. For example, the spent silicon contact mass can be collected in a hopper under an inert gas atmosphere such as a nitrogen atmosphere. Alternatively, it can be conveyed directly to a thermal treatment zone shortly after it is generated under direct process conditions. Suitable means for heating the spent silicon contact mass to an appropriate temperature as previously defined are, for example, a calcining furnace or a rotary kiln.

Although a temperature of between about 250° C. to 800° C. can be used to treat the spent silicon spent contact mass, a temperature of about 300° C. to 600° C. is preferred and a temperature of about 300° C. to 400° C. is particularly preferred. Duration of treatment can vary in the range of from about 0.2 to 1 hour depending upon the temperature employed, the efficiency of gas-solid contact, and the specific characteristics of the spent contact mass. The stored powder after it has been treated can be recycled to an organohalosilane reactor. If desired the treated spent contact mass can be introduced into the reactor with makeup powdered silicon along with additional proper catalyst and metallic promoters in a batchwise or continuous manner. A fixed bed or fluid bed reactor can be used.

In order that those skilled in the art will be better able to practice the present invention, the following example is given by way of illustration and not by way of limitation. All parts are by weight unless otherwise indicated.

EXAMPLE

Oxidized spent silicon contact mass was prepared in a glass stirred bed reactor by passing air at a rate of 150 cc per minute over a 50 g charge of spent contact mass. The glass stirred bed reactor was operated over a period of 2 hours at 300° C. and 1 atmosphere. The spent silicon contact mass was obtained from a methylchlorosilane reactor which utilized a copper catalyst and a promoter, such as a mixture of zinc and tin. An exotherm of 50°-80° C. which was generated in the stirred powder bed, indicated that oxidation had taken place.

A mixture was prepared consisting of about one part of the above prepared oxidized spent silicon contact mass, about 4 parts of fresh silicon having an average particle size in the range of from 0.1 to 200 microns, and sufficient copper/brass catalyst to provide a copper content in the resulting mixture of about 5.1% by weight. The resulting contact mass was contacted with methylchloride flowing at about 90 scc/min following the same procedure as described above.

The following shows the results obtained with respect to the silanes collected, where "T/D" means the weight ratio of methyltrichlorosilane to dimethyldichlorosilane in the collected product, "Silicon Yield" means the conversion to chlorosilane based on the original weight of the contact mass mixture, and "Activity" means rate of chlorosilane produced based on weight of contact mass.

TABLE 1

| Silicon Yield (g/g) | Activity (mg/g/hr) | T/D |
|---|---|---|
| 0.008 | 136 | 0.229 |
| 0.075 | 236 | 0.148 |
| 0.142 | 277 | 0.107 |
| 0.209 | 204 | 0.088 |
| 0.267 | 174 | 0.085 |
| 0.297 | 153 | 0.079 |

Oxidized spent contact mass free of added fresh copper and powdered silicon was then used for methylchlorosilane production. The contact mass was prepared as described above. Fifty grams of the treated contact mass was contacted with 90 cc per minute of flowing methylchloride at 300° C. for 4 hours. The following results were obtained:

TABLE 2

| Silicon Yield (g/g) | Activity (mg/g/hr) | T/D |
|---|---|---|
| 0.054 | 166 | 0.576 |
| 0.061 | 35 | 0.916 |
| 0.070 | 34 | 1.105 |

The above results show that oxidized spent contact mass provides substantially less selectivity and activity for methylchlorosilane production as compared to oxidized spent contact mass used in combination with fresh copper catalyst and fresh silicon powder. However, when the oxidized spent contact mass was diluted with 67% of fresh silicon powder, it showed an increase in both activity and an improvement in selectivity as shown by the following results:

TABLE 3

| Silicon Yield (g/g) | Activity (mg/g/hr) | T/D |
|---|---|---|
| 0.021 | 96 | 0.138 |
| 0.066 | 187 | 0.097 |
| 0.119 | 187 | 0.080 |
| 0.181 | 155 | 0.075 |
| 0.225 | 134 | 0.072 |

The above results show the effectiveness of the treated spent contact mass as catalyst for methylchlorosilane synthesis.

Although the above results are directed to only a few of the very many variables which can be employed in the practice of the method of the present invention, it should be understood that the present invention is directed to a much broader variety of spent silicon contact mass treated in accordance with the practice of the invention as set forth in the description preceding this example.

What is claimed is:

1. A process for making organohalosilanes by the direct method, comprising effecting reaction between an organic halide and a mixture comprising silicon powder, an effective amount of direct method catalyst, and spent direct method contact mass which has been in an oxygen containing atmosphere under conditions sufficient to render it substantially nonreactive in air at temperatures up to 350° C., where the resulting treated spent direct method contact mass is used directly or in combination with silicon powder and direct method catalyst in an amount sufficient to maintain during organohalosilane production, from about 0.1 to about 10% by weight of copper relative to silicon.

2. A process in accordance with claim 1, where the organic halide is methylchloride.

3. A batch process for making organohalosilane, in accordance with claim 1.

4. A continuous process for making organohalosilane, in accordance with claim 1.

5. A process in accordance with claim 1, using a fixed bed reactor.

6. A process in accordance with claim 1, using a copper-zinc-tin catalyst.

7. A process in accordance with claim 1, using a fluid bed reactor.

* * * * *